United States Patent
Sugiyama et al.

(10) Patent No.: US 8,758,587 B2
(45) Date of Patent: Jun. 24, 2014

(54) ANALYSIS APPARATUS AND ANALYSIS METHOD

(75) Inventors: Koji Sugiyama, Kyoto (JP); Daisuke Matsumoto, Kyoto (JP); Yasunori Shiraki, Kyoto (JP); Satoshi Yonehara, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 522 days.

(21) Appl. No.: 13/217,790

(22) Filed: Aug. 25, 2011

(65) Prior Publication Data
US 2012/0048734 A1    Mar. 1, 2012

(30) Foreign Application Priority Data

Aug. 25, 2010  (JP) ................................ 2010-188102
Aug. 5, 2011   (JP) ................................ 2011-171910

(51) Int. Cl.
*G01N 27/447*    (2006.01)
*G01N 27/453*    (2006.01)
*G01N 30/04*     (2006.01)
*G01N 30/24*     (2006.01)

(52) U.S. Cl.
USPC ............... 204/451; 204/601; 422/70; 422/50

(58) Field of Classification Search
CPC .................. G01N 30/04; G01N 30/61–30/24; G01N 1/00; G01N 35/00; G01N 35/10–35/1097; G01N 35/08–35/085; G01N 35/00584–35/0095; G01N 27/447–27/44752
See application file for complete search history.

(56) References Cited

U.S. PATENT DOCUMENTS 3,925,207 A * 12/1975 Scriba ........................ 210/138
6,491,816 B2 * 12/2002 Petro .............................. 506/43
2007/0175757 A1  8/2007 Hanafusa et al. ............ 204/451

FOREIGN PATENT DOCUMENTS

JP   2005-214710   8/2005   .......... G01N 27/447
WO   WO 01/16587   3/2001   ............ G01N 27/26

OTHER PUBLICATIONS

European Extended Search Report for European Application No. 11178826.1 (mailed Dec. 2, 2011).

* cited by examiner

*Primary Examiner* — Alex Noguerola
(74) *Attorney, Agent, or Firm* — Morgan, Lewis & Bockius LLP

(57) ABSTRACT

An analysis apparatus is provided with a storage tank, an injection nozzle, a syringe, a collection nozzle, a test sample tank, a microchip having two or more separation channels, detectors, a waste liquid tank, a controller, and a power supply. The collection nozzle collects a specimen which becomes a test sample from a test sample container housing the specimen, and transfers the specimen to the test sample tank. The separation channels separate characteristic components contained in the test sample. The injection nozzle is distanced from the collection nozzle and injects the test sample from the test sample tank into the separation channels. The detectors detect the separated characteristic components in the separation channels.

17 Claims, 8 Drawing Sheets

CONTROLLER

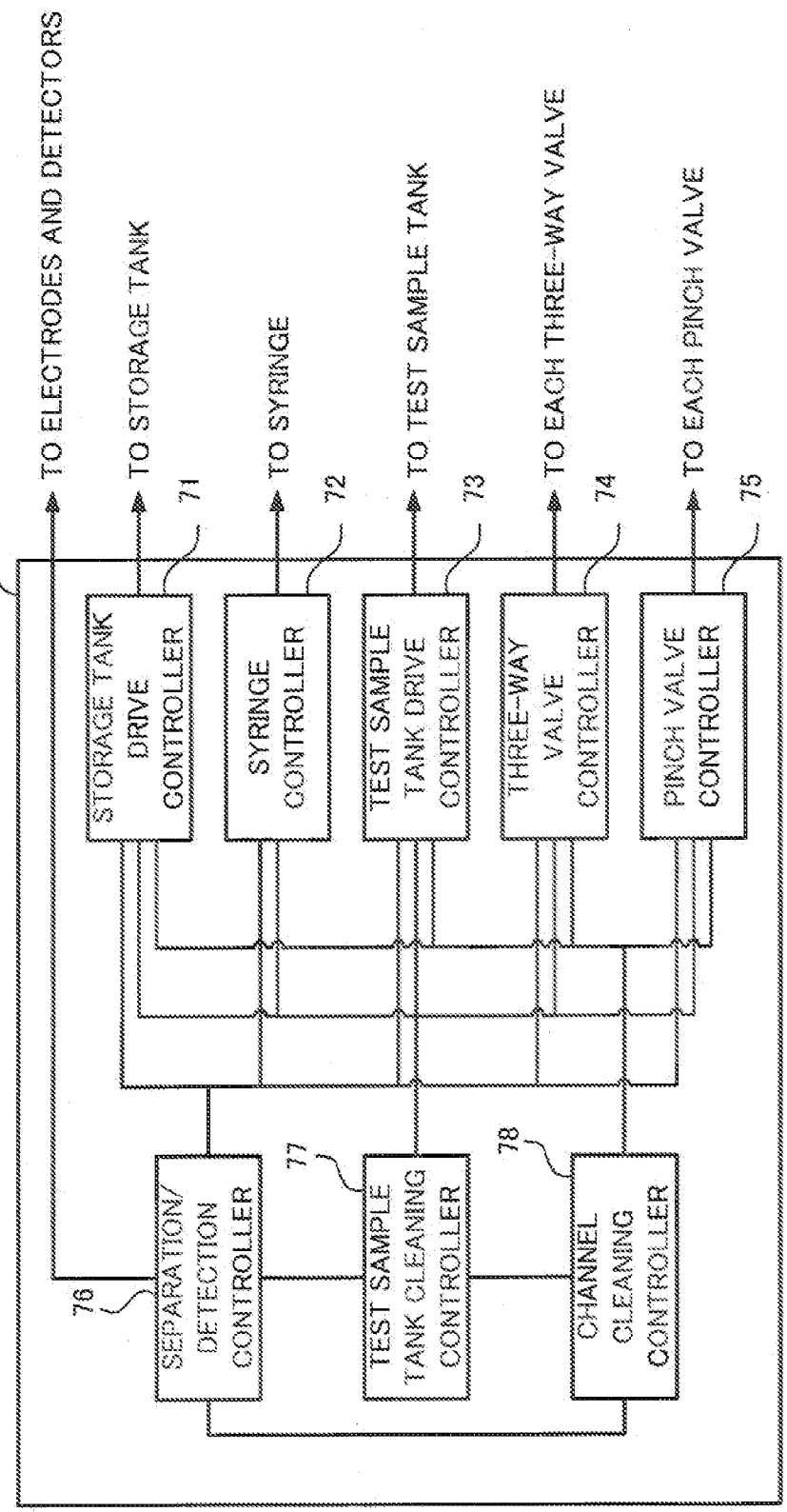

ANALYSIS APPARATUS AND ANALYSIS METHOD

CROSS-REFERENCE TO RELATED APPLICATION

This application claims the benefit of Japanese Patent Application No. 2010-188102, filed Aug. 25, 2010, and Japanese Patent Application No. 2011-171910, filed Aug. 5, 2011, the entire disclosure of which are incorporated by reference herein.

FIELD

The present invention relates to an analysis apparatus and an analysis method.

BACKGROUND

Among analysis methods for analyzing the concentrations or quantities of characteristic components included in a test sample, there is a method that includes a separating step wherein the characteristic components are separated from the test sample, and a detecting step wherein the separated, characteristic components is detected. For example, in an analysis method that uses capillary electrophoresis, a separation channel with a comparatively small cross-section is filled with an electrophoretic liquid, and a test sample is also introduced into one end of a separation channel. When a voltage is applied to both ends of the separation channel, an electroosmotic flow occurs whereby the electrophoretic liquid moves from the positive side to the negative side due to electrophoresis, for example. Also, due to the voltage being applied, the characteristic components attempt to move according their respective electrophoretic mobility. Consequently, the characteristic components move according a velocity vector obtained by combining the velocity vector of electroosmotic flow with the velocity vector of motion due to electrophoresis. According to this movement, the characteristic components are separated from other components. By detecting the separated characteristic components with optical techniques, for example, the quantities and concentrations of characteristic components can be analyzed.

Unexamined Japanese Patent Application KOKAI Publication No. 2005-214710 describes a microchip treating method and apparatus able to raise the rate of operation of electrophoretic separation while also setting a separation buffer liquid and electrophoresis parameters for individual test samples. With such technology, the dispensing unit of the apparatus is shared, and a separation buffer liquid and test samples are injected into electrophoresis channels of a microchip with the dispensing unit. The separation buffer liquid injected into one end of the electrophoresis channels fills the electrophoresis channels due to a separation buffer filler/discharger. A high-voltage power supply for electrophoresis independently applies an electrophoretic voltage to each electrophoresis channel. When separation buffer liquid filling and test sample injection into one electrophoresis channel is finished, the apparatus proceeds to separation buffer solution filling and test sample injection into the next electrophoresis channel. For electrophoresis channels finished with test sample injection, an electrophoretic voltage is applied, and electrophoretic separation as well as detection operations by a fluorometer are initiated.

SUMMARY

With the microchip treating method in Unexamined Japanese Patent Application KOKAI Publication No. 2005-214710, channels for an analysis process are plurally provided and successive test sample measurement is conducted to raise the rate of operation of electrophoretic separation. However, since the pre-processing time including filling with solution for analysis and introducing test samples is not considered, the analysis process overall takes time.

Also, in the case where blood samples are taken as the targets of analysis and measurement, there is a risk that cleaning will be time-consuming given the comparatively high viscosity of blood samples. Furthermore, the handling of blood samples requires care due to problems of sanitation management and safety improvement.

The present invention, being devised in light of the foregoing circumstances, takes as an object to provide an analysis apparatus and an analysis method able to shorten the time required for analysis, including pre-processing steps.

An analysis apparatus in accordance with a first aspect of the present invention is provided with a collecting unit that collects a specimen from a specimen container and transfers the collected specimen to a test sample tank where the specimen is processed into a test sample, two or more influx units into which the test sample flows in, a dispensing unit, distanced from the collecting unit, that injects the test sample from the test sample tank into the influx units, processing units that process the test sample flowing into the influx units, and a detecting unit that detects characteristic components contained in the test sample in the influx units.

An analysis method in accordance with a second aspect of the present invention is an analysis method conducted by an analysis apparatus that analyzes characteristic components contained in a test sample, the analysis method including a collecting step that collects a specimen from a specimen container with a collecting unit, a treating step that transfers the specimen collected in the collecting step to a test sample tank and processes the specimen into the test sample inside the test sample tank, an injecting step that injects the test sample from the test sample tank into two or more influx units with a dispensing unit distanced from the collecting unit, a processing step that processes the test sample injected into the influx units in the injecting step, and a detecting step that detects characteristic components contained in the test sample processed in the processing step.

BRIEF DESCRIPTION OF THE DRAWINGS

A more complete understanding of this application can be obtained when the following detailed description is considered in conjunction with the following drawings, in which:

FIG. 3 is a block diagram illustrating an exemplary configuration of a controller in accordance with an embodiment;

DETAILED DESCRIPTION

Embodiment

Figure 1:
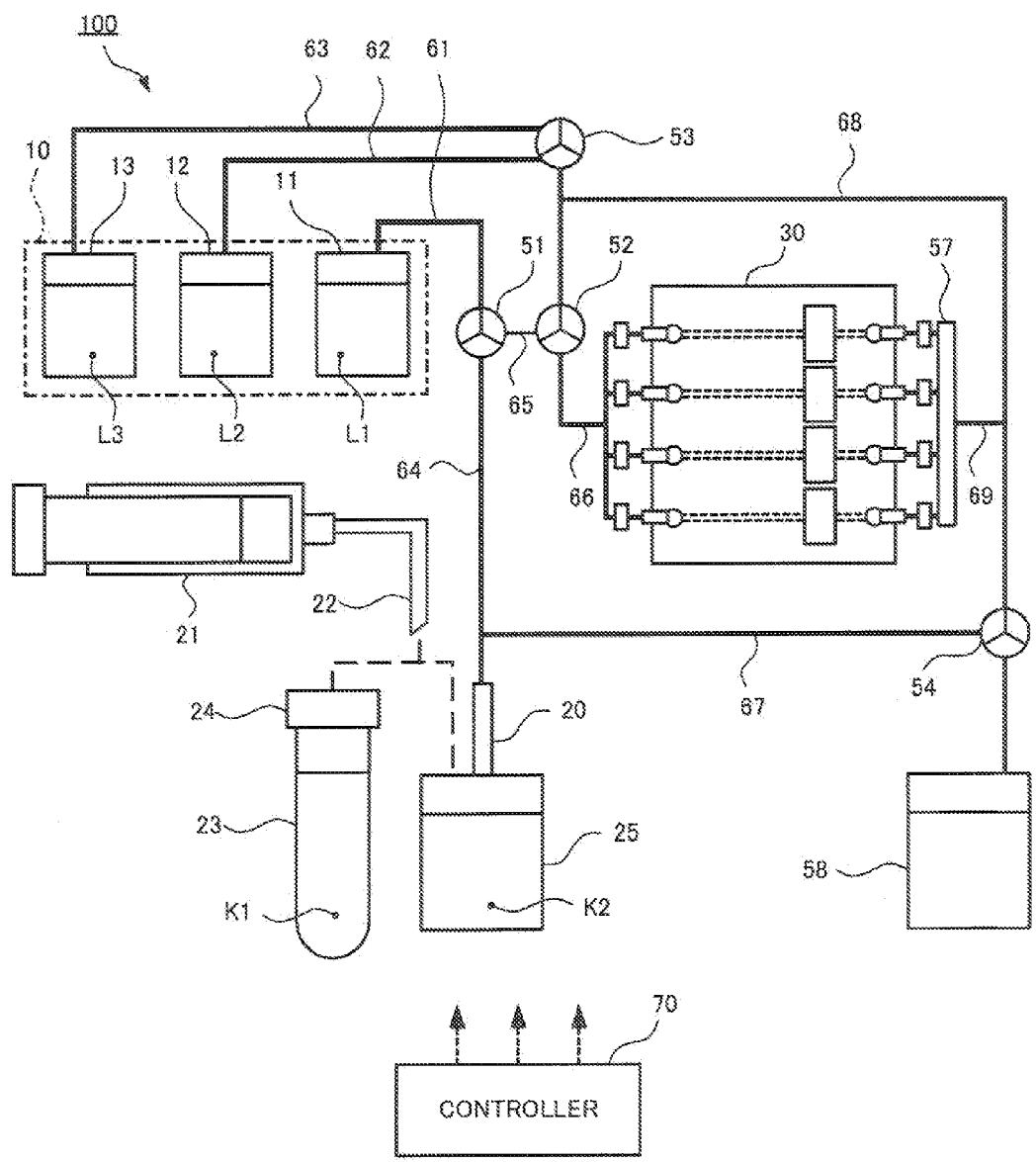
FIG. 1 is a schematic configuration of an analysis apparatus in accordance with an embodiment of the present invention.
Figure 2:
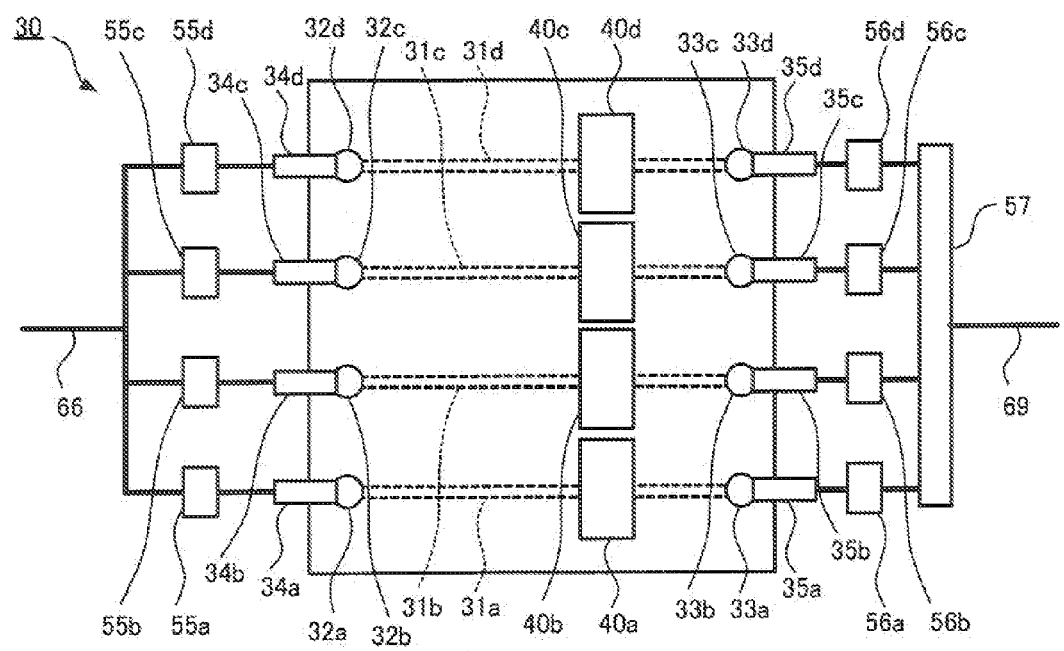
FIG. 2 is a schematic configuration of the main separation unit of the analysis apparatus according to FIG. 1.

FIG. 1 is a schematic configuration of an analysis apparatus in accordance with an embodiment of the present invention. As an example, a case will be described wherein an analysis apparatus 100 is an analysis apparatus that conducts analysis by capillary electrophoresis and which has four separation channels. FIG. 2 is a schematic configuration of the main separation unit of the analysis apparatus according to FIG. 1. In the present embodiment, the analysis apparatus 100 will be explained while supposing the case of using capillary electrophoresis to analyze a specimen of blood, etc. collected from an organism.

The analysis apparatus 100 is provided with a storage tank 10, an injection nozzle (injection unit) 20, a syringe 21, a collection nozzle 22, a test sample tank 25, a microchip (main separation unit) 30, detectors 40, a waste liquid tank 58, a controller 70, and a power supply. The microchip 30 is provided with separation channels 31, induction apertures 32, discharge apertures 33, electrodes 34, and electrodes 35. In FIG. 1, wiring from the controller 70 to the respective units is omitted in order to ease comprehension and avoid confusion in the drawing. Herein, the separation channels 31a, 31b, 31c, and 31d may be collectively referred to as the separation channels 31, the induction apertures 32a, 32b, 32c, and 32d as the induction apertures 32, the discharge apertures 33a, 33b, 33c, and 33d as the discharge apertures 33, the electrodes 34a, 34b, 34c, and 34d as the electrodes 34, the electrodes 35a, 35b, 35c, and 35d as the electrodes 35, and the detectors 40a, 40b, 40c, and 40d as the detectors 40, respectively.

The storage tank 10 is provided with an electrophoretic liquid tank 11, a purified water tank 12, and a cleaning liquid tank 13. An electrophoretic liquid L1 is stored in the electrophoretic liquid tank 11. The electrophoretic liquid L1 is a liquid that functions as a buffer, and may be 100 mM malic acid and arginine buffer (pH 5.0) plus 1.5% chondroitin sulfate C sodium salt, for example. Purified water L2 is stored in the purified water tank 12. A cleaning liquid L3 is stored in the cleaning liquid tank 13. The electrophoretic liquid tank 11, the purified water tank 12, and the cleaning liquid tank 13 are each provided with a pump (not illustrated), which causes internally stored liquid to flow into channels 61, 62, and 63. Operation of the pumps in the storage tank 10 is controlled by the controller 70.

A configuration is also possible wherein a syringe pump is connected to a three-way valve 51 or 53 as the pumps in the storage tank 10, for example. In this case, the three-way valve 51 or 53 communicates each tank with the syringe pump and suctioning is conducted with the syringe pump. Then, the three-way valve 51 or 53 communicates the syringe pump with a channel 64, 65, or 68, and liquid can be sent into the channel 64, 65, or 68 by causing the syringe pump to conduct an ejection operation.

Three-way valves 51, 52, and 53 are provided in order to switch the channels circulating the respective liquids from the channels 61, 62, and 63 to the channels 64, 65, 66, and 68. Also, a three-way valve 54 is provided in order to switch the channels flowing from the channels 67, 68, and 69 to the waste liquid tank 58. Channel switching of the three-way valves 51, 52, 53, and 54 is controlled by the controller 70.

The specimen used in this specification is not limited to a specific substance, and a specimen in aqueous solution, a specimen from an organism, food, a culture fluid of bacteria, etc., or a liquid extract from plant matter, etc. may be used. Proteins, substances in the body, or substances in blood may be given as examples of the substance to be analyzed that is included in a test sample in this specification. Hemoglobin, albumin, globulin, or enzymes may be given as specific examples of proteins. Glycated hemoglobins, variant hemoglobins, minor hemoglobins, or modified hemoglobins may be given as examples of hemoglobin, and more specifically, hemoglobin A0 (HbA0), stable hemoglobin A1c (HbA1c), unstable HbA1c, hemoglobin A2 (HbA2), hemoglobin S (HbS, sickle-cell hemoglobin), hemoglobin F (HbF, fetal hemoglobin), hemoglobin M (HbM), hemoglobin C (HbC), methemoglobin, carbaminohemoglobin, or acetyl hemoglobin may be given. The enzymes may be amylase, alkaline phosphatase, γ-glutamyltransferase, lipase, creatine kinase, lactate dehydrogenase, glutamic oxaloacetic transaminase, or glutamic pyruvate transaminase.

Bilirubin, hormones, metabolites, nucleotide chains, chromosomes, peptide chains, carbohydrate antigens, glycans, lipids, or tumor marker protein antigens may be given as specific examples of substances in the body or substances in blood. Thyroid stimulating hormone, corticosteroids, chorionic gonadotropin, insulin, glucagon, adrenal medullary hormone, estrogen, progesterone, aldosterone, or cortisol may be given as examples of hormones. Oligonucleotide chains or polynucleotide chains may be given as examples of nucleotide chains, while C-peptide or angiotensin I may be given as examples of peptide chains. AFP, hCG, transferrin, IgG, thyroglobulin, CA19-9, prostate specific antigen, or tumor marker carbohydrate antigens having special glycans that produce cancer cells may be given as examples of carbohydrate antigens. Besides the above, the specimen may be proteins, peptides, or carbohydrate antigens derived from microorganisms, or various allergens causing allergies (such as house dust, ticks, pollen from cedar, cypress, ragweed, etc., animals such as prawns or crabs, food such as egg whites, fungus, insects, medicines, or allergens derived from chemical substances, etc.).

Hereinafter, explanation of samples that include characteristic components for analyzing with the analysis apparatus 100 will be divided into a specimen K1 and a test sample K2. The specimen K1 refers to a subject of inspection that has been collected from an organism, for example, and refers to a sample in an unprocessed state. The test sample K2 refers to a sample ready for measurement and analysis using the analysis apparatus 100, which has been obtained by processing a specimen K1 with given methods, such as diluting it in solution or mixing it with other substances, for example. To take one case as an example, the specimen K1 may be whole blood, while the sample K2 may be obtained by diluting the whole blood specimen K1 to a given concentration in a solution that includes hemolytic components which exhibit hemolytic action destroying blood cell membranes. The characteristic component subjected to measurement may be hemoglobin.

The syringe 21 suctions and ejects liquid from an aperture to which the collection nozzle 22 is joined. The collection nozzle 22 is the portion that suctions or ejects the specimen K1 due to the suctioning or discharging operation of the syringe 21.

The collection nozzle 22 has a tip formed to be able to penetrate the cap 24 of a test sample container 23, and is able to collect the specimen K1 inside the test sample container 23. The collection nozzle 22 is able to penetrate and collect the specimen K1 without unsealing the cap 24 of the test sample container 23.

It is necessary for the collection nozzle 22 to have a given strength for penetrating the test sample container 23 (herein referring to the cap 24), to additionally be in a form able to suction and eject the specimen K1, and to additionally be in a form able to transfer the specimen K1. The collection nozzle 22 is formed in the shape of a long, thin, tubular needle out of a metal such as stainless steel, ceramic, or a plastic material. For example, a syringe needle may be used. In order to more easily penetrate the test sample container 23, it is preferable for the collection nozzle 22 to have a sharp shape by providing a taper angle at the tip of the collection nozzle 22 or diagonally cutting the tip. Also, in order to reduce friction during penetration, it is preferable for the collection nozzle 22 to have a smooth surface.

The cap 24 of the test sample container 23 may also be processed into a state that facilitates a penetration process by the collection nozzle 22. For example, the cap 24 may be made of a material such as elastic rubber and be able to maintain a closed state such that the liquid, etc. inside does not leak out in the case where no external force is applied, but wherein a microscopic aperture communicating the interior of the test sample container 23 with the outside is formed by a needle. By creating such a microscopic hole with the collection nozzle 22, the force applied when penetrating into the test sample container 23 can be reduced, and a penetration process into the test sample container 23 with the collection nozzle 22 can be performed easily.

The collection nozzle 22 is supported by a driving mechanism not illustrated. Due to this driving mechanism, the collection nozzle 22 can be inserted into and drawn out from the test sample container 23 and made to enter and exit the test sample tank 25. With the driving operation of the collection nozzle 22 and the suctioning and discharging operations of the syringe 21, a specimen K1 collected from the test sample container 23 can be transferred to the test sample tank 25. The suctioning and discharging operations of the syringe 21 and the driving of the collection nozzle are controlled by the controller 70.

The test sample tank 25 has functions such that given processing such as diluting with a diluting solution or mixing with other substances can be performed inside the tank and a specimen K1 can be brought into a state suitable for analysis, or in other words, processed into a test sample K2. The test sample tank 25 is provided with a pump similarly to the storage tank 10, which causes the test sample K2 inside flow into the channels 64 and 67 via the injection nozzle 20. Alternatively, the injection nozzle 20 may be provided with a suction pump which causes the test sample K2 to flow into the channels 64 and 67. Operation of a pump for the test sample tank 25 or the injection nozzle 20 is controlled by the controller 70. A configuration is also possible wherein a syringe pump is connected to the three-way valve 51 or 54 as the pump for the test sample tank 25, for example. The action of the syringe pump in this case is similar to the case of the storage tank 10.

The microchip (main separation unit) 30 is the site where analysis using capillary electrophoresis is conducted. The microchip 30 is formed using silica as its material, for example. The material of the microchip 30 may also be acrylic, etc. Hereinafter, a configuration of the microchip (main separation unit) 30 will be explained.

FIG. 2 is a schematic configuration of the main separation unit of the analysis apparatus according to FIG. 1. The microchip 30 is provided with separation channels 31a, 31b, 31c, and 31d. The configuration of each of the separation channels 31a, 31b, 31c, and 31d is the same. The separation channel 31a will be explained as a representative example.

The separation channel 31a is a microscopic channel formed in the microchip 30, in which separation for analysis using capillary electrophoresis is conducted. The cross-section of the separation channel 31a is preferably circular with a diameter from 25 μm to 100 μm or rectangular with sides of length from 25 μm to 100 μm, but not limited thereto, and any shape and dimensions suitable for conducting capillary electrophoresis may be used. Also, although the length of the separation channel 31a is approximately 30 mm in the present embodiment, the length is not limited thereto.

The separation channel 31a is provided with an induction aperture 32a, a discharge aperture 33a, an electrode 34a, and an electrode 35a. Also, a detector 40a is provided corresponding to this separation channel 31a. Furthermore, pinch valves 55a and 56a are provided in order to select the separation channel 31a as the subject of analysis from among a plurality of separation channels. The opening and closing of the pinch valves 55a and 56a are controlled by the controller 70.

In the case where the inside of the separation channel 31a is filled with a liquid such as the electrophoretic liquid L1, for example, first the three-way valve 52 is switched, and the liquid flows into the channel 66. According to instructions from the controller 70, the pinch valve 55a is opened in order to communicate just the channel joined to the separation channel 31a. Contemporaneously with the opening of the pinch valve 55a, the pinch valve 56a positioned on the other side of the separation channel 31a is opened according to instructions from the controller 70. By opening the pinch valve 56a, the separation channel 31a communicates with the channel 69. Liquid flows into the channel 69 and joins with the waste liquid tank 58 via the three-way valve 54.

In order to suppress imbalances in the load applied among the respective separation channels 31a, 31b, 31c, and 31d, it is preferable for the separation channel 31a to be provided with a manifold 57 between the pinch valve 56a and the channel 69.

The respective separation channels 31a, 31b, 31c, and 31d of the microchip 30 are independently controlled by the controller 70. When selecting one of the separation channels 31a, 31b, 31c, or 31d as an analysis target, the controller 70 conducts control so as to open the corresponding pinch valve 55a, 55b, 55c, or 55d and the pinch valve 56a, 56b, 56c, or 56d, thus introducing a test sample K2 into the respective separation channel 31a, 31b, 31c, or 31d from the respective induction aperture 32a, 32b, 32c, or 32d, which is discharged from the respective discharge aperture 33a, 33b, 33c, or 33d. Also, the controller 70 controls with instructions for the application of voltage to a respective electrode 34a, 34b, 34c, or 34d and the respective electrode 35a, 35b, 35c, or 35d, the separation of characteristic components by electrophoresis with the respective separation channel 31a, 31b, 31c, or 31d, and detection of the concentration and quantity of a characteristic component with the respective detector 40a, 40b, 40c, or 40d.

FIG. 2 illustrates an example wherein respective detectors 40a, 40b, 40c, and 40d corresponding to the respective separation channels 31a, 31b, 31c, and 31d are provided. It is sufficient to have at least one of the detectors 40a, 40b, 40c, and 40d which detects characteristic components separated into the respective separation channels 31a, 31b, 31c, and 31d. For example, it may also be designed such that detection is conducted for a plurality of separation channels 31 with a single detector 40, such as by providing two detectors 40a and 40b wherein the detector 40a detects the separation channels 31a and 31b, while the detector 40b detects the separation channels 31c and 31d.

Induction apertures 32 and discharge apertures 33 are formed in the separation channels 31. The induction apertures 32 are formed on one end of the separation channels 31, and are the portions through which a test sample K2 is introduced by the injection nozzle 20. Also, besides a test sample K2, introduction of electrophoretic liquid L1, purified water L2, and cleaning liquid L3 is possible in the present embodiment. The discharge apertures 33 are provided on the other end of the separation channels 31, and are the portions through which a test sample K2, electrophoretic liquid L1, purified water L2, and cleaning liquid L3, etc. filling the separation channels 31 are discharged.

Also, electrodes 34 and electrodes 35 are provided on either end of the separation channels 31. In the present embodiment, the electrodes 34 are exposed to the induction apertures 32, while the electrodes 35 are exposed to the discharge apertures 33.

The detectors 40 are for analyzing characteristic components separated from a test sample K2 in the separation channels 31. The detectors 40 are provided along the separation channels 31 at a portion closer to the discharge apertures 33 than the induction apertures 32. The detectors 40 are respectively provided with a light source and a light sensor, for example. Light from the light source is incident on a test sample K2, and the light passing through the test sample K2 is sensed by the light sensor, thereby measuring the absorbance of the test sample K2. Then, the characteristic components can be analyzed from the absorbance of the test sample K2.

Operation of the respective units of the analysis apparatus 100 discussed above are controlled by the controller 70. Analysis is conducted by the analysis apparatus 100 according a series of controls. The controller 70 is for example made up of a CPU, memory, an input/output interface, etc.

Three-way valves 51, 52, 53, and 54 are provided in the analysis apparatus 100. The three-way valves 51, 52, 53, and 54 each have three connections, with the communicative and blocked states of these connections being independently controlled by the controller 70.

The electrophoretic liquid tank 11 is connected to the three-way valve 51 via the channel 61. The purified water tank 12 and the cleaning liquid tank 13 are connected to the three-way valve 53 via the channels 62 and 63. The test sample tank 25 is connected to the three-way valve 51 via the channel 64, and also connected to the three-way valve 54 via the channel 67. The three-way valve 51 is connected to the three-way valve 52 via the channel 65. The three-way valve 53 is connected to the three-way valves 52 and 54 via the channel 68.

The separation channels 31 are connected to the downstream side of the three-way valve 52 via the channel 66. Channel switching of the three-way valve 52 can be controlled by the controller 70 to allow or block flow into the separation channels 31. The separation channels 31 are connected to the three-way valve 54 via the channel 69. Channel switching of the three-way valve 54 is controlled by the controller 70, and the communicative and blocked states with the separation channels 31 are independently controlled. The waste liquid tank 58 is joined to the downstream side of the three-way valve 54. The waste liquid tank 58 is for storing used liquid. The waste liquid tank 58 may also be provided with a pump that suctions internal gas. By suctioning gas in the waste liquid tank 58 with a pump, liquid in the channel 67 or the channels 68 and 69 can be suctioned into the waste liquid tank 58.

The power supply (not illustrated) is for applying a voltage for conducting analysis by capillary electrophoresis in the separation channels 31, and is connected to the electrodes 34 which are the positive electrodes and the electrodes 35 which are the negative electrodes. The applied voltage is approximately 1.5 kV, for example, and functions may also be provided such that the positive electrodes and the negative electrodes apply opposite polarities.

FIG. 3 is a block diagram illustrating an exemplary configuration of a controller in accordance with an embodiment. FIG. 3 illustrates a configuration of the controller 70 in FIG. 1. The controller 70 is provided with a storage tank drive controller 71, a syringe controller 72, a test sample tank drive controller 73, a three-way valve controller 74, a pinch valve controller 75, a separation/detection controller 76, a test sample tank cleaning controller 77, and a channel cleaning controller 78.

The storage tank drive controller 71 controls the flow rate of liquid flowing through the channels 61, 62, and 63 by controlling the pumps of the electrophoretic liquid tank 11, the purified water tank 12, and the cleaning liquid tank 13. The syringe controller 72 controls the suction and discharge operations of the syringe 21 and controls driving of the collection nozzle. The test sample tank drive controller 73 controls the quantity of liquid flowing from the test sample tank into the channel 64 or 67 via the injection nozzle by controlling the pump of the test sample tank.

The three-way valve controller 74 switches the pathways of liquid flowing through the channels 61 to 69 by controlling the three-way valves 51, 52, 53, and 54. The pinch valve controller 75 individually controls the open/close operations of the pinch valves 55a to 55d and 56a to 56d.

The separation/detection controller 76 introduces electrophoretic liquid L1 and a test sample K2 into the separation channels 31 by causing the electrophoretic liquid tank 11, the purified water tank 12, the syringe 21 and collection nozzle 22, the test sample tank 25, the three-way valves 51 and 52, as well as the pinch valves 55a to 55d and 56a to 56d to operate in cooperation with each other. Then, the separation/detection controller 76 applies a voltage to the electrodes 34 and the electrodes 35, and controls the detectors 40 to analyze the characteristic components of a test sample K2, for example. The separation and detection controller causes the electrophoretic liquid tank 11, the purified water tank 12, the syringe 21 and collection nozzle 22, the test sample tank 25, the three-way valves 51 and 52, as well as the pinch valves 55a to 55d and 56a to 56d to operate via the storage tank drive controller 71, the syringe controller 72, the test sample tank drive controller 73, the three-way valve controller 74, and the pinch valve controller 75.

The test sample tank cleaning controller 77 cleans the collection nozzle 22 and the test sample tank 25 by causing the storage tank 10, the syringe 21 and collection nozzle 22, the test sample tank 25, and the three-way valves 51, 52, 53, and 54 to operate in cooperation with each other. The test sample tank cleaning controller 77 causes the storage tank 10, the syringe 21 and collection nozzle 22, the test sample tank 25, and the three-way valves 51, 52, 53, and 54 to operate via the storage tank drive controller 71, the syringe controller 72, the test sample tank drive controller 73, the three-way valve controller 74, and the pinch valve controller 75.

The channel cleaning controller 78 cleans the channel 66 and the separation channels 31a to 31d by causing the storage tank 10, the three-way valves 51, 52, 53, and 54, as well as the pinch valves 55a to 55d and 56a to 56d to operate in cooperation with each other. The channel cleaning controller 78 causes the storage tank 10, the three-way valves 51, 52, 53, and 54, as well as the pinch valves 55a to 55d and 56a to 56d to operate via the storage tank drive controller 71, the test sample tank drive controller 73, the three-way valve controller 74, and the pinch valve controller 75.

The controller 70 may be realized by a computer and a program running thereon as discussed earlier. It is also possible to realize the respective units of the controller 70 as logical circuits. Hereinafter, analysis and cleaning operations will be explained.

Figure 4A:
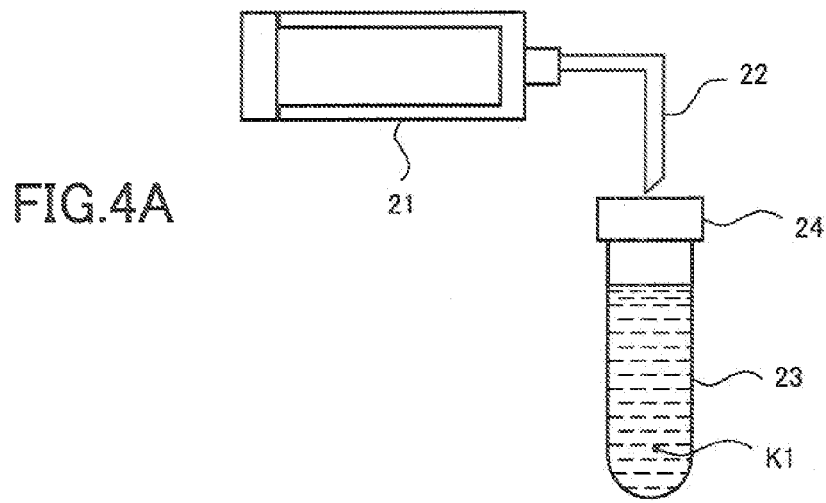
FIG. 4A illustrates a state before suctioning a specimen into a syringe.
Figure 4B:
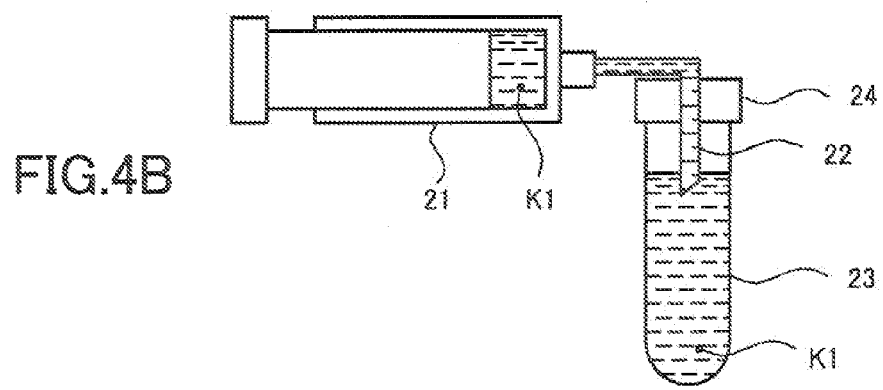
FIG. 4B illustrates a state after suctioning a specimen into a syringe.
Figure 4C:
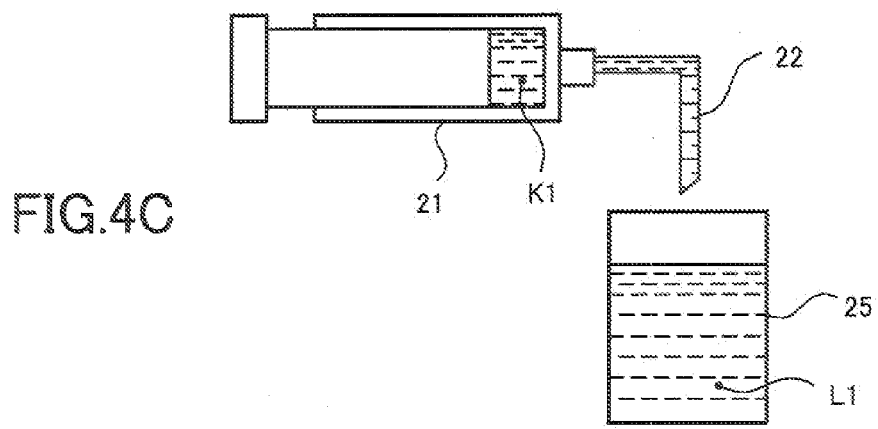
FIG. 4C illustrates a state of transferring a specimen into a test sample tank.
Figure 4D:
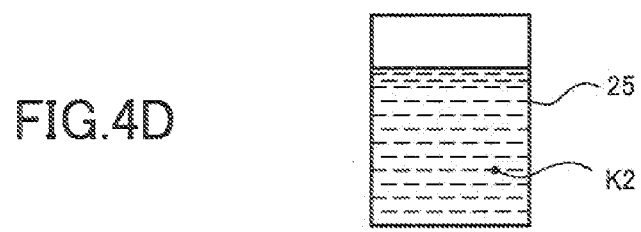
FIG. 4D illustrates a state after processing a specimen into a test sample in a test sample tank.

FIGS. 4A to 4D are schematic diagrams illustrating steps for preparing a test sample in the analysis apparatus in accordance with FIG. 1. First, the collection nozzle 22 is made to penetrate the cap 24 by the driving mechanism (not illustrated) discussed earlier according to instructions from the controller 70 (see FIG. 4A). Then, the tip of the collection nozzle 22 is immersed in a specimen K1 and the syringe 21 is made to suction (see FIG. 4B). After suctioning the specimen K1, the collection nozzle 22 is moved to the test sample tank 25 and the syringe 21 is made to discharge. The specimen K1 suctioned into the syringe 21 via the collection nozzle 22 is ejected towards and transferred to the test sample tank 25 where electrophoretic liquid L1 is stored, for example (see FIG. 4C). After that, a test sample K2 is prepared by adjusting the inside of the test sample tank 25 to a given dilution concentration and mixing thoroughly, etc. (FIG. 4D). In order to facilitate mixing of the test sample K2, or in other words agitation between the specimen K1 and the electrophoretic liquid L1, it is preferable to make the syringe 21 repeatedly suction and discharge.

The injection nozzle 20 is able to suction the test sample K2 from the test sample tank 25 and inject it into the separation channels 31. The injection nozzle 20 may be of any shape or material, as long as it is separately provided and distanced from the collection nozzle 22 and able to pour a test sample K2 into the separation channels 31.

The section in which a test sample K2 is suctioned from the test sample tank 25 and injected into the separation channels 31 with the injection nozzle 20 is collectively designated the dispensing unit. The dispensing unit includes the channels 64, 65, and 66 as well as the injection nozzle 20. In the present embodiment, the channels 64 and 65 as well as the injection nozzle 20 are also used to clean the 25. In the strict sense, the dispensing unit is the channel 66.

Figure 5:
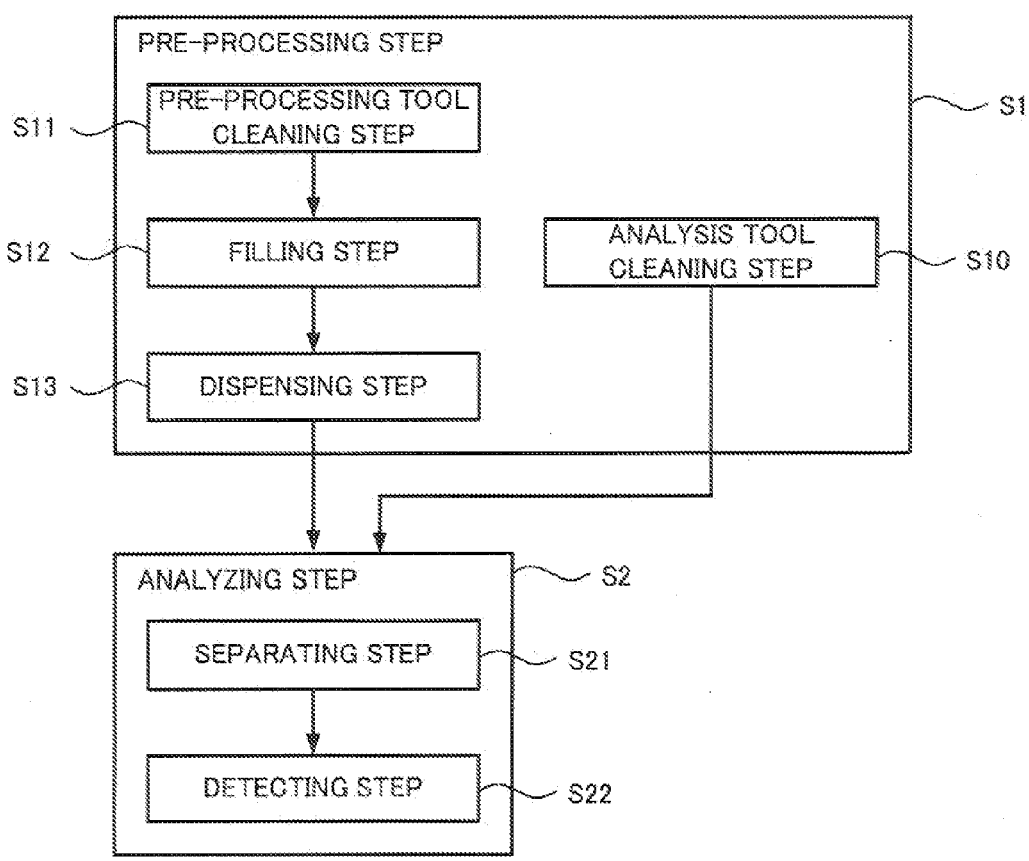
FIG. 5 is a flowchart illustrating exemplary steps in an analysis method in accordance with an embodiment.

Hereinafter, an analysis method using an analysis apparatus 100 will be explained using FIGS. 1 to 5. FIG. 5 is a flowchart illustrating an exemplary analysis method in accordance with an embodiment. The steps of the analysis method are broadly divided into a pre-processing step S1 and an analyzing step S2.

In the present embodiment, the specimen K1 is taken to be whole blood while the test sample K2 is taken to be a solution of diluted whole blood including hemoglobin in its characteristic components, for example. The test sample K2 subjected to analysis by the analysis apparatus 100 is taken to be obtained by diluting the specimen K1 to a given concentration with electrophoretic liquid L1. The electrophoretic liquid L1 includes hemolytic components which exhibit hemolytic action destroying blood cell membranes, thereby putting the test sample K2 in a state suited to hemoglobin analysis.

The test sample container 23 uses an evacuated blood collection tube, while the cap 24 refers to a rubber stopper, etc. that seals the aperture of the evacuated blood collection tube. The collection nozzle 22 of the syringe 21 for penetrating the cap 24 uses a stainless steel syringe needle, etc.

The pre-processing step (step S1) is made up of a pre-processing tool cleaning step (step S11), a filling step (step S12), a dispensing step (step S13), and an analysis tool cleaning step (step S10). Pre-processing tools include the syringe 21, the collection nozzle 22, the test sample tank 25, the injection nozzle 20, and the channels 64 and 65. Analysis tools include the separation channels 31.

The pre-processing tool cleaning step (step S11), the filling step (step S12), and the dispensing step (step S13) of the pre-processing step (step S1) are made up of consecutive steps. The analysis tool cleaning step (step S10) of the pre-processing step (step S1) is independently configured. The consecutive operations made up of step S11 to step S13 and the operation in step S10 do not affect each other. For this reason, the operations from step S11 to step S13 and the operation in step S10 may at least partially overlap in their times of execution, and it is possible to simultaneously execute the operations from step S11 to S13 and in step S10. Hereinafter, details will be explained.

The analysis tool cleaning step (step S10) precedes the analyzing step (step S2) and involves cleaning away a test sample K2, etc. used in the last analysis and still remaining in the separation channels 31. First, the three-way valve 53 is switched to communicate the purified water tank 12 and the cleaning liquid tank 13 with the channel 68 according to instructions from the channel cleaning controller 78 of the controller 70. Also, the three-way valve 52 is switched to communicate the channel 68 with the channel 66. Furthermore, the three-way valve 54 is switched to communicate from the channel 68 to the waste liquid tank 58. In this state, the interiors of the separation channels 31 are cleaned by filling the separation channels 31 with purified water L2 and cleaning liquid L3 and then discharging into the waste liquid tank 58. Herein, purified water L2 may be made to flow after cleaning with the cleaning liquid L3, and the fill-discharge sequence may also be executed multiple times.

The pre-processing tool cleaning step (step S11) is the step conducted first in the pre-processing step (step S1), and in the case of consecutively using the analysis apparatus 100, is the step that cleans the pre-processing tools used last time. First, the three-way valve 51 is switched to close the channel 64 according to instructions from the test sample tank cleaning controller 77 of the controller 70. The three-way valve 54 is switched to communicate the channel 67 with the waste liquid tank 58. Then, any test sample K2 remaining in the test sample tank 25 is discharged into the waste liquid tank 58. Next, the three-way valves 51, 52, and 53 are switched to communicate the purified water tank 12 and/or the cleaning liquid tank 13 with the test sample tank 25 via the channels 68, 65, and 64. The test sample tank 25 is filled with purified water L2 and/or cleaning liquid L3. Then, the collection nozzle 22 is placed into the liquid in the test sample tank 25, and suction-discharge is performed several times. Next, the liquid in the test sample tank 25 is again discharged into the waste liquid tank 58. In so doing, the syringe 21, the collection nozzle 22, the test sample tank 25, the injection nozzle 20, and the channels 64, 65, and 67 are cleaned. The filling with purified water L2 and/or cleaning liquid L3, the suctioning-discharging of the collection nozzle 22, and the discharging of liquid may also be conducted multiple times.

The filling step (step S12) is the step of filling the separation channels 31 with electrophoretic liquid L1 in order to realize electrophoresis. The three-way valve 51 is switched to communicate the channel 61 with the channel 65 and block the channel 64 therefrom according to instructions from the controller 70. The three-way valve 52 is switched to communicate the channel 65 with the channel 66 and block the channel 68 therefrom. By switching the three-way valve 54, the channel 68 communicates with the waste liquid tank 58. In this state, the separation channels 31 are filled with electrophoretic liquid L1.

The dispensing step (step S13) is the step of dispensing a test sample K2 from the induction apertures 32 into the separation channels 31. Also, the dispensing step (step S13) in the present embodiment includes a step of processing a specimen K1 into a test sample K2, by diluting a specimen K1 and taking the result as a test sample K2 and putting in a state suited for analysis, for example.

In the step of the dispensing step (step S13) that processes a specimen K1 into a test sample K2 by dilution and puts it into a state suited for analysis, the three-way valve 51 is switched to communicate the channel 61 with the channel 64 in advance. Electrophoretic liquid L1 is introduced into the test sample tank 25, and the electrophoretic liquid L1 is used to dilute the specimen K1 to a given concentration. The liquid used when diluting is not limited to electrophoretic liquid L1, and purified water L2 may also be used, depending on the analysis parameters. Also, depending on the analysis parameters, a step of mixing with other substances, thorough mixing, and putting a sample in to a state suited to other analysis may also be conducted in the test sample tank 25.

In the step of the dispensing step (step S13) that processes a specimen K1 into a test sample K2 by dilution, first, the collection nozzle 22 is made to penetrate the cap 24 by the driving mechanism (not illustrated) discussed earlier, according to instructions from the controller 70 (see FIG. 4A). Then, the tip of the collection nozzle 22 is immersed in a specimen K1 and the syringe 21 is made to suction (see FIG. 4B). The syringe 21 is made to discharge the specimen K1 suctioned into the syringe 21 via the collection nozzle 22, which is ejected towards and transferred to the test sample tank 25 where electrophoretic liquid L1 is stored, for example (see FIG. 4C). After that, a series of process to prepare a test sample K2 is conducted, which may involve adjusting the inside of the test sample tank 25 to a given dilution concentration and mixing thoroughly, etc. (FIG. 4D). In order to facilitate mixing of the test sample K2, or in other words agitation between the specimen K1 and the electrophoretic liquid L1, it is preferable to make the syringe 21 repeatedly suction and discharge.

Subsequently, the diluted test sample K2 in the test sample tank 25 is suctioned with the injection nozzle 20, inserted into the induction apertures 32 of the separation channels 31, and the test sample K2 is introduced into the separation channels 31. Thus, the pre-processing step S1 ends, and the apparatus enters a state where analysis is possible in the separation channels 31.

Herein, a diluting step is included in the dispensing step (step S13) in the present embodiment, but in the case where a test sample K2 not requiring dilution is the subject of analysis, or in other words in the case of taking a specimen K1 directly as the subject of analysis, the dispensing step (step S13) may be performed without conducting a diluting step. Also, when processing a specimen K1 into a test sample K2, a treatment processing step may be conducted as appropriate rather than a diluting step in the case where processing other than dilution is required. In any case, the collection nozzle 22 and the injection nozzle 20 are distanced from each other, and collection of the specimen K1 and dispensing of the test sample K2 can be conducted in parallel.

When the pre-processing step (step S1) ends, the analyzing step (step S2) is executed. The analyzing step (step S2) is made up of a separating step (step S21) and a detecting step (step S22).

The separating step (step S21) is the step of separating characteristic components included in a test sample K2 in a electrophoretic liquid L1 filling the separation channels 31. According to instructions from the controller 70, a voltage is applied to the positive electrodes 34 and the negative electrodes 35 from a power supply, and electroosmotic flows from the electrodes 34 to the electrodes 35 are produced in the electrophoretic liquid L1. At this point, movement from the electrodes 34 towards the electrodes 35 is induced in the characteristic components according to their intrinsic electrophoretic mobility.

The detecting step (step S22) is the step of detecting the quantity or concentration, etc. of the separated characteristic components. According to instructions from the controller 70, the detectors 40 illuminate a specific position along the separation channels 31 with light having a wavelength of 415 nm from light sources, for example, and receive the transmitted light with light sensors. When characteristic components pass through the specific position along the separation channels 31, the light received by the light sensors (i.e., its absorbance) changes, and by this change the concentration and quantity of characteristic components can be detected. The analysis results are stored in a storage unit (not illustrated), for example, and the detecting step (step S22) ends. According to the above steps, the pre-processing step (step S1) and the analyzing step (step S2) end, and analysis using the analysis apparatus 100 is completed.

Figure 6:
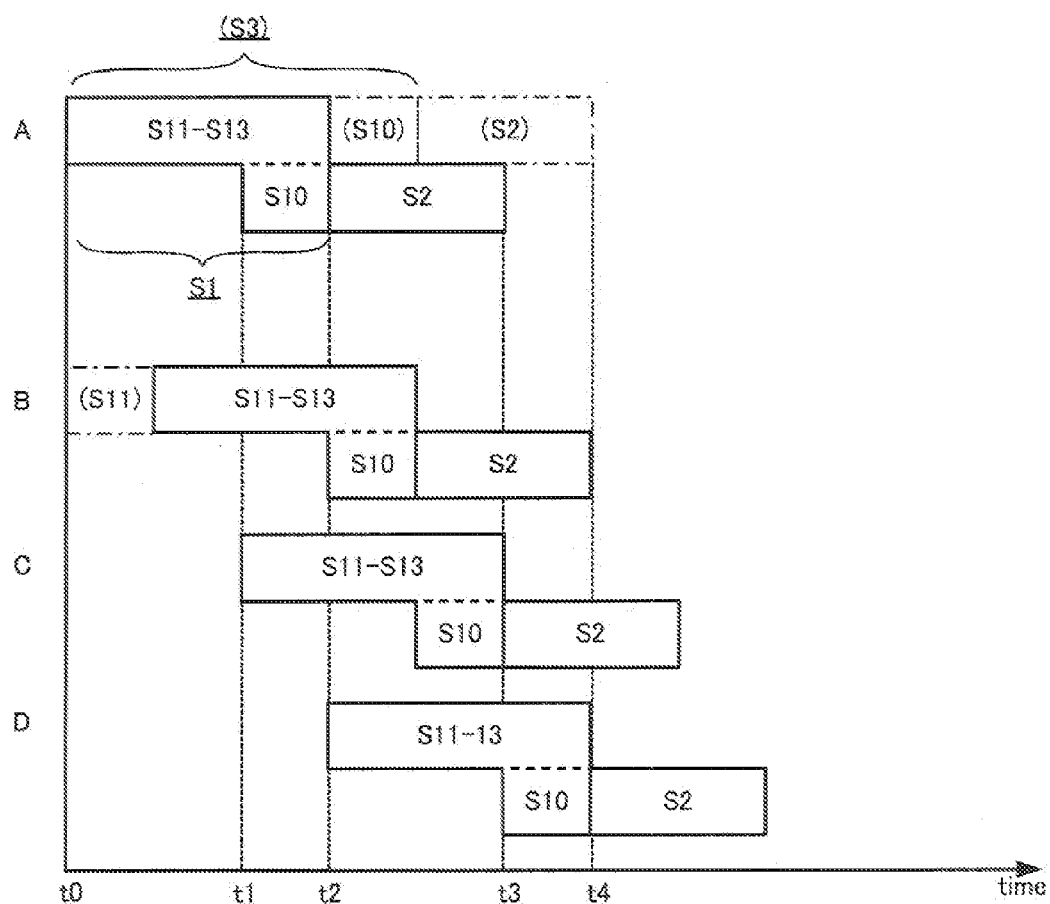
FIG. 6 is a timing chart illustrating exemplary processing times of an analysis method in accordance with an embodiment.

FIG. 6 is a timing chart illustrating exemplary processing times of an analysis method in accordance with an embodiment. For the analysis method, refer to the analysis method in accordance with the embodiment illustrated in FIG. 5.

Regarding the respective processes conducted in the respective separation channels 31$a$, 31$b$, 31$c$, and 31$d$ of the microchip 30, processing times conducted in the separation channel 31$a$ are illustrated with the chart A, processing times conducted in the separation channel 31$b$ with the chart B, processing times conducted in the separation channel 31$c$ with the chart C, and processing times conducting in the separation channel 31$d$ with the chart D, respectively. Similarly processing is taken to be conducted for all charts A, B, C, and D, and additionally, the times involved in processing are taken to be nearly equal.

The case of four separation channels 31 will be explained. Although the respective separation channels 31$a$, 31$b$, 31$c$, and 31$d$ are independently controlled, the channels 61 to 69 are shared except for the paths from the pinch valves 55 to the pinch valves 56 via the respective separation channels 31$a$, 31$b$, 31$c$, and 31$d$.

For this reason, in the case of individually using respective separation channels 31$a$, 31$b$, 31$c$, and 31$d$, it is necessary to stagger times without conducting steps simultaneously such that the processing times for the respective separation channels 31$a$, 31$b$, 31$c$, and 31$d$ do not overlap when introducing a specific analysis sample into the separation channel 31$a$ from the test sample tank 25 that differs from the other separation channels 31$b$, 31$c$, and 31$d$, for example. Also, in the case where there is a risk of mixing among the analysis samples using in the respective separation channels 31$a$, 31$b$, 31$c$, and 31$d$, and also in the case of the pre-processing tool cleaning step (step S11) conducted in the respective separation channels 31$a$, 31$b$, 31$c$, and 31$d$, processing cannot be conducted simultaneously, and it is necessary to stagger times such that the processing times do not overlap.

In some cases it is not necessary to conduct processing by staggering times such that the processing times do not overlap. For example, there is the case of the step that fills the respective separation channels 31$a$, 31$b$, 31$c$, and 31$d$ with the same liquid (step S12). In step S12, it is necessary to fill the respective separation channels 31a, 31b, 31c, and 31d as well as the channels 61 to 69 with electrophoretic liquid L1. Furthermore, since the electrophoretic liquid L1 is shared, processing can be conducted such that the times at least partially overlap. In some cases, it is also possible to conduct processing simultaneously.

As an example, the first separation channel 31 will be explained given the chart A by example. The chart A demonstrates that a time t4 is required until all steps are complete in the case of consecutively executing all steps. In contrast, by conducting the operation in step S10 in parallel with the operations in step S11 to step S13, processing is completed in a time t3, thus demonstrating that the time until processing is complete can be shortened to less than the time t4 by the amount of time taken by step S10 (the difference between the time t2 and the time t1).

According to the reasons discussed above, at least part of the pre-processing step (step S1) in the separation channel 31a and the separation channel 31b can be processed such that their times overlap. Also, at least part of the pre-processing step (step S1) in the separation channel 31b and separation channel 31c, and the separation channel 31c and the separation channel 31d can be processed such that their times overlap.

Furthermore, at least part of the analyzing step (step S2) in the separation channel 31a and the separation channel 31b can be processed such that their times overlap. Also, at least part of the analyzing step (step S2) in the separation channel 31b and the separation channel 31c or in the separation channel 31c and the separation channel 31d can be similarly processed such that their times overlap, respectively.

More specifically, the case of consecutively processing the separation channel 31a (chart A) and the separation channel 31b (chart B) will be explained. Since the pre-processing tool cleaning step (step S11) for the separation channel 31a and the pre-processing tool cleaning step (step S11) for the separation channel 31b cannot be processed simultaneously, the separation channel 31 is placed in a standby state unable to initiate steps until the pre-processing tool cleaning step (step S11) ends for the separation channel 31a. When the pre-processing tool cleaning step (step S11) for the separation channel 31a ends, the pre-processing tool cleaning step (step S11) for the separation channel 31b is initiated. For the steps thereafter, or in other words for part of the pre-processing steps (step S10, step S12, and step S13) and the analyzing step (step S2), the steps for the separation channel 31a and the separation channel 31b can be processed even if their processing times overlap.

As a result, in the case of consecutively processing a plurality of separation channels 31 in an analysis apparatus 100, analysis can be conducted such that the times for at least part of the pre-processing steps, herein being the time during the pre-processing tool cleaning step (step S11), do not overlap.

For each of the separation channels 31a, 31b, 31c, and 31d, the time taken by their respective analysis processes can be shortened, and can be processed such that at least part of the time taken by the respective analysis processes overlap. For this reason, the time taken for analysis in an analysis apparatus 100 can be greatly shortened.

Figure 7:
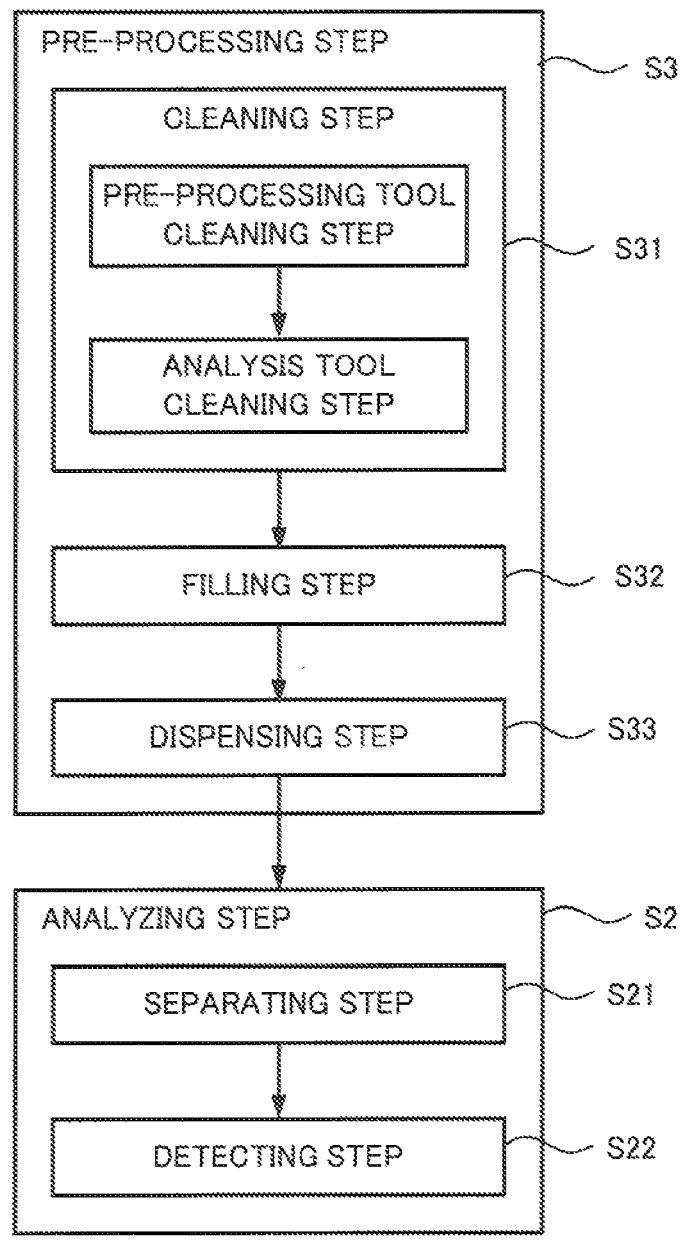
FIG. 7 is a flowchart illustrating an exemplary analysis method of the related art.

FIG. 7 is a flowchart illustrating an exemplary analysis method of the related art. Although the analyzing step (step S1) is similar to that of an analysis apparatus 100 in accordance with the present embodiment, the pre-processing step (step S3) includes a pre-processing tool and analysis tool cleaning step (step S31), a filling step (step S32), and a dispensing step (step S33).

This is equivalent to the case of conducting the analysis tool cleaning step (step S10) after the pre-processing tool cleaning step (step S11) and then conducting the filling step (step S12) and the dispensing step (step S13) in the case of an analysis apparatus 100 in accordance with the present embodiment, and demonstrates that in an analysis method of the related art, the pre-processing step (step S3) requires the total time from step S10 to step S13. The time taken by the pre-processing step (step S3) is indicated as the sum of the difference between the time t2 and the time t1 with the time t2 in the timing chart in FIG. 6.

Figure 8:
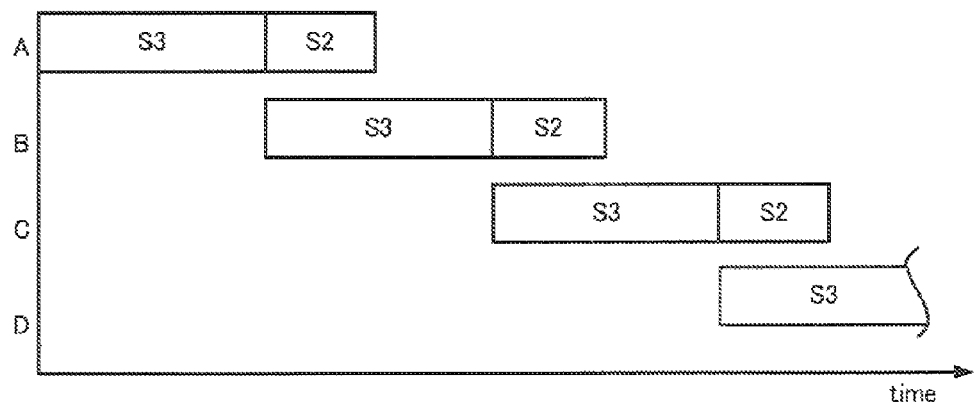
FIG. 8 is a timing chart illustrating exemplary processing times of an analysis method of the related art.
Figure 9:
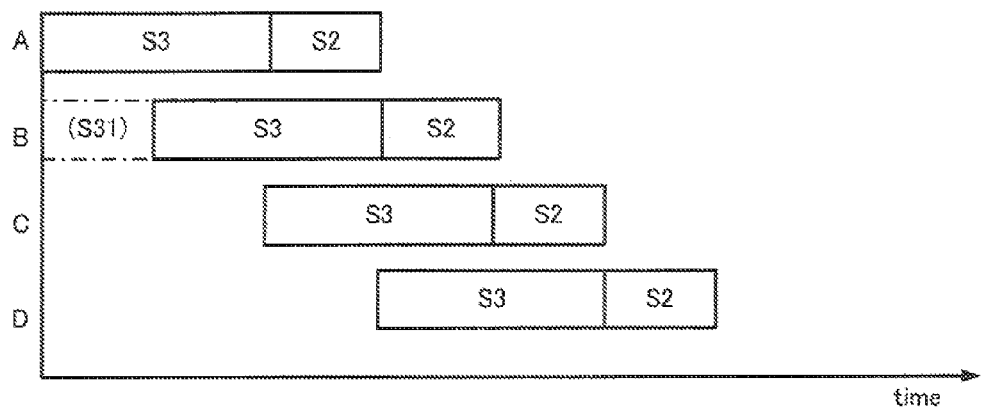
FIG. 9 is a timing chart illustrating exemplary processing times in accordance with a modification of an analysis method of the related art.

FIGS. 8 and 9 are timing charts illustrating exemplary processing times of analysis methods of the related art. For the analysis method, refer to the analysis method flowchart illustrated in FIG. 7.

FIG. 8 is a timing chart for the case where the pre-processing step (step S3) is finished for the separation channel 31a, and then the analyzing step (step S2) is initiated while simultaneously initiating the pre-processing step (step S3) for the next separation channel 31b, with the consecutive processing being conducted similarly for the respective separation channels 31a, 31b, 31c, and 31d.

As explained in FIG. 7, in the pre-processing step (step S3), since each step is conducted in order without overlapping, the time itself taken by the pre-processing step (step S3) for the respective separation channels 31a, 31b, 31c, and 31d is longer than that of the present embodiment. Also, the time taken until processing between the respective separation channels 31a, 31b, 31c, and 31d, or in other words the respective standby times for the separation channels 31a, 31b, 31c, and 31d, is longer. For this reason, FIG. 8 demonstrates that the time taken by the processing overall is much longer compared to the case of an analysis apparatus 100 in accordance with the present embodiment.

FIG. 9 is a timing chart for the case where pre-processing step (step S3) for the separation channel 31a is partially finished, and then the pre-processing step (step S3) for the next separation channel 31b is initiated before initiating the analyzing step (step S2) for the separation channel 31a, with the consecutive processing being conducted similarly for the respective separation channels, 31a, 31b, 31c, and 31d.

During the pre-processing step for each of the separation channels 31a, 31b, 31c, and 31d, conducting processing that at least partially overlaps in time is similar to the case of an analysis apparatus 100 in accordance with the present embodiment. In the steps in FIG. 9, analysis can be conducted such that part of the pre-processing step, herein being the times between cleaning steps (step S31), do not overlap. FIG. 9 demonstrates that the time taken by the processing overall is shortened compared to the case in FIG. 8 by the amount that the standby times for the respective separation channels 31a, 31b, 31c, and 31d are shortened.

A comparison of an analysis method in accordance with an embodiment of the present invention in FIG. 6 against the case of an analysis method of the related art in FIG. 9 first demonstrates that, when viewing the respective separation channels 31a, 31b, 31c, and 31d, the processing time for each separation channel 31 is shortened by an amount equivalent to the analysis tool cleaning step (step S10) in an analysis method in accordance with an embodiment of the present invention.

Also, in both an analysis method in accordance with an embodiment of the present invention in FIG. 6 and an analysis method of the related art in FIG. 9, analysis can be conducted such that part of the pre-processing steps do not overlap in time. However, if the standby times until initiating the step for the next separation channel 31 are compared, the analysis method in FIG. 9 requires standby for the time taken by a cleaning step (step S31) that includes a pre-processing tool cleaning step and an analysis tool cleaning step, whereas an analysis method in accordance with an embodiment of the present invention requires standby only for the time taken by a pre-processing tool cleaning step (step S11). Since the time taken by step S31 is the sum of the time taken by the analysis tool cleaning step (step S10) and the time taken by the pre-processing tool cleaning step (step S11), in the method in FIG. 9 the standby time increases by an amount equivalent to the analysis tool cleaning step (step S10). In an analysis method in accordance with an embodiment of the present invention, the standby time until initiating the step for the next separation channel 31 can be shortened by an amount equivalent to the analysis tool cleaning step (step S10).

As a result, the above demonstrates that, in the case of using an analysis apparatus 100 in accordance with the present embodiment, standby times are shorter, the processing times for each of the separation channels 31a, 31b, 31c, and 31d (i.e., the time corresponding to the serial flow from the pre-processing step to the analyzing step) are shorter, and the overall processing is conducted more efficiently.

As explained above, according to an analysis apparatus and an analysis method in accordance with the present embodiment, the time required to process and analyze can be shortened such that at least part of the pre-processing step and the analyzing step overlap in time.

By doing work using different nozzles for the collection nozzle and the injection nozzle, processing can be conducted such that the step which includes preparing a test sample and the step which includes analyzing a test sample at least partially overlap in time. For this reason, it is possible to overlap processing times and shorten the overall processing time required for analysis from the pre-processing step to the analyzing step, thereby improving efficiency. Also, by plurally providing separation channels for use when analyzing, processing can be conducted in parallel, shortening the overall processing time.

As a result, in addition to shortening the processing times for the respective separation channels, the respective processing times for the separation channels can be made to overlap, making it possible to analyze samples more efficiently.

Furthermore, since different nozzles are provided for the collection nozzle and the injection nozzle, material properties suited for each function can be selected. For example, a hard material with a tip formed in a sharp shape such as a syringe needle is desirable for the collection nozzle, whereas the material properties and shape are not particularly limited for the injection nozzle, as long as a test sample can be injected into a separation channel.

The collection nozzle is able to penetrate the test sample container and directly collect a test sample, which saves the trouble of unsealing the cap on the test sample container. Also, in the case where the test sample is whole blood and the test sample container is an evacuated blood collection tube, there has been a risk of infection, etc. due to splattering or blood, since the work of collection a test sample from an evacuated blood collection tube and unsealing an evacuated blood collection tube is done directly with a syringe by hand. However, with the present embodiment it becomes possible to process everything with an analysis apparatus, thereby improving safety. Furthermore, since anything beyond the required amount of test sample remains in the test sample container, disposal or other post-processing can be easily and safely conducted without splattering.

In an embodiment, the case of a microchip provided with four separation channels was described, but a greater number of separation channels may also be provided. Also, a case was given by example where one test sample tank was provided for a test sample subjected to measurement, but there may be plural test sample tanks, and may be arbitrarily designed to match various parameters such as the time taken to prepare a test sample to be used, the time taken to clean tools to be used, the time taken for separation and measurement, and the number of separation channels, etc.

In an embodiment, an analysis apparatus that analyzes by capillary electrophoresis was described by way of example, but an analysis apparatus is not limited to the foregoing example. For example, rather than simply separating characteristic components included in a test sample, processing such as mixing and extraction or chemical reactions and immunoreactions may be conducted in the influx units (influx channels) where processing is conducted. Particularly, it is preferable to perform processing involved with various reactions suited to processing in microscopic channels provided in a microchip.

An analysis apparatus and analysis method in accordance with the present embodiment is not limited to the foregoing examples. A specific configuration of an analysis apparatus and an analysis method in accordance with the present invention may be freely subject to various design modifications. For example, it is possible to arbitrarily set factors such as the channel design, the number of storage tanks, the position where each functional unit is disposed, and the form of each function.

The number of separation channels is not limited to four. The configuration of the separation channels is not limited to what are called straight channels, and may also be cross-injection channels where two channels intersect each other, for example. The test sample is not limited to a sample containing hemoglobin typified by whole blood, and may also contain DNA, RNA (ribonucleic acid), and proteins, for example.

The analysis conducted in an analyzing step in the present invention is not limited to analysis using capillary electrophoresis, and may also use small-sample chromatography, for example. In this case, in the separating step, separation, elution, reaction, etc. is performed in columns, while in the detecting step, reaction product is detected.

Otherwise, the following configuration are included in ideal modifications of the present invention.

An analysis apparatus in accordance with a first aspect of the present invention is preferably provided with a first cleaning unit (77) that cleans the collecting unit (22) and the test sample tank (25), and a second cleaning unit (78) that cleans the dispensing unit (66) and the influx units (31).

Preferably, the first cleaning unit (77) cleans the collecting unit (22) and the test sample tank (25) such that the time during which the dispensing unit (66) injects the test sample into the influx units (31), the time during which the test sample is processed by the processing units (34, 35), and the time during which characteristic components contained in the test sample are detected by the detecting unit (40) at least partially overlap in time.

Preferably, the second cleaning unit (78) cleans the dispensing unit (66) and the influx units (31) such that the time during which the collecting unit (22) transfers the specimen into the test sample tank (25) and the time during which the specimen is processed into a test sample in the test sample tank (25) at least partially overlap in time.

Preferably, the specimen container (23) is sealed such that the specimen does not leak out, the collecting unit (22)

includes a collecting nozzle (22), and the collecting nozzle (22) collects the specimen by penetrating part of the specimen container (23).

Preferably, the specimen container (23) is an evacuated blood collection tube, and the collecting nozzle (22) collects the specimen by penetrating a sealing unit of the evacuated blood collection tube.

Preferably, the influx units (31) are a microchip (30) having channels.

Preferably, the processing units (34, 35) include separating units (34, 35) that separate characteristic components contained in the test sample, and the detecting unit (40) detects characteristic components that have been separated by the separating units (34, 35).

Preferably, the influx units (31) include the separating units (34, 35), and the separating units (34, 35) conduct electrophoresis.

An analysis method in accordance with a second aspect of the present invention preferably includes a first cleaning step that cleans the collecting unit (22) and the test sample tank (25), and a second cleaning step that cleans the dispensing unit (66) and the influx units (31).

Preferably, the time during which the first cleaning step is conducted and the time during which the injecting step, the processing step, and the detecting step are conducted at least partially overlap in time.

Preferably, the time during which the second cleaning step is conducted and the time during which the collecting step and the treating step are conducted at least partially overlap in time.

Preferably, the influx units (66) includes separating units (34, 35) that separate characteristic components contained in the test sample, and the processing step includes a separating step that separates the test sample injected into the influx units (66) into characteristic components contained in the test sample with the separating units (34, 35).

Preferably, the separating step separates characteristic components contained in the test sample using electrophoresis.

Having described and illustrated the principles of this application by reference to one or more preferred embodiments, it should be apparent that the preferred embodiments may be modified in arrangement and detail without departing from the principles disclosed herein and that it is intended that the application be construed as including all such modifications and variations insofar as they come within the spirit and scope of the subject matter disclosed herein.

What is claimed is:

1. An analysis apparatus comprising:
    a collecting unit that collects a specimen from a specimen container and transfers the collected specimen to a test sample tank where the specimen is processed into a test sample;
    two or more influx units into which the test sample flows in;
    a dispensing unit, distanced from the collecting unit, that injects the test sample from the test sample tank into the influx units;
    processing units that process the test sample flowing into the influx units; and
    a detecting unit that detects characteristic components contained in the test sample in the influx units.

2. The analysis apparatus according to claim 1, further comprising:
    a first cleaning unit that cleans the collecting unit and the test sample tank; and
    a second cleaning unit that cleans the dispensing unit and the influx units.

3. The analysis apparatus according to claim 2, wherein the first cleaning unit cleans the collecting unit and the test sample tank such that the time during which the dispensing unit injects the test sample into the influx units, the time during which the test sample is processed by the processing units and the time during which characteristic components contained in the test sample are detected by the detecting unit at least partially overlap in time.

4. The analysis apparatus according to claim 3, wherein the second cleaning unit cleans the dispensing unit and the influx units such that the time during which the collecting unit transfers the specimen into the test sample tank and the time during which the specimen is processed into a test sample in the test sample tank at least partially overlap in time.

5. The analysis apparatus according to claim 2, wherein the second cleaning unit cleans the dispensing unit and the influx units such that the time during which the collecting unit transfers the specimen into the test sample tank and the time during which the specimen is processed into a test sample in the test sample tank at least partially overlap in time.

6. The analysis apparatus according to claim 1, wherein the specimen container is sealed such that the specimen does not leak out, the collecting unit includes a collecting nozzle, and the collecting nozzle collects the specimen by penetrating part of the specimen container.

7. The analysis apparatus according to claim 6, where the specimen container is an evacuated blood collection tube, and the collecting nozzle collects the specimen by penetrating a sealing unit of the evacuated blood collection tube.

8. The analysis apparatus according to claim 1, wherein the influx units are a microchip having channels.

9. The analysis apparatus according to claim 1, wherein the processing units include separating units that separate characteristic components contained in the test sample, and the detecting unit detects characteristic components that have been separated by the separating units.

10. The analysis apparatus according to claim 9, wherein the influx units include the separating units, and the separating units conduct electrophoresis.

11. An analysis method conducted by an analysis apparatus that analyzes characteristic components contained in a test sample, the analysis method comprising:
    a collecting step that collects a specimen from a specimen container with a collecting unit;
    a treating step that transfers the specimen collected in the collecting step to a test sample tank and processes the specimen into the test sample inside the test sample tank;
    an injecting step that injects the test sample from the test sample tank into two or more influx units with a dispensing unit distanced from the collecting unit;
    a processing step that processes the test sample injected into the influx units in the injecting step; and
    a detecting step that detects characteristic components contained in the test sample processed in the processing step.

12. The analysis method according to claim 11, further comprising:
    a first cleaning step that cleans the collecting unit and the test sample tank; and
    a second cleaning step that cleans the dispensing unit and the influx units.

13. The analysis method according to claim 12, wherein the time during which the first cleaning step is conducted and the time during which the injecting step, the processing step, and the detecting step are conducted at least partially overlap in time.

14. The analysis method according to claim 13, wherein the time during which the second cleaning step is conducted and the time during which the collecting step and the treating step are conducted at least partially overlap in time.

15. The analysis method according to claim 12, wherein the time during which the second cleaning step is conducted and the time during which the collecting step and the treating step are conducted at least partially overlap in time.

16. The analysis method according to claim 11, wherein the influx units include separating units that separate characteristic components contained in the test sample, and the processing step includes a separating step that separates the test sample injected into the influx units into characteristic components contained in the test sample 17. The analysis method according to claim 16, wherein the separating step separates characteristic components contained in the test sample by using electrophoresis.

* * * * *